US009752977B2

(12) United States Patent
Balmond et al.

(10) Patent No.: US 9,752,977 B2
(45) Date of Patent: Sep. 5, 2017

(54) CORROSION SENSOR

(71) Applicant: BAE SYSTEMS plc, London (GB)

(72) Inventors: Mark David Balmond, Filton (GB);
Mark Alcuin Venables, Filton (GB);
Ian Michael Sturland, Filton (GB);
Alan Peter Pritchard, Dyfed (GB)

(73) Assignee: BAE SYSTEMS plc, London (GB)

( * ) Notice: Subject to any disclaimer, the term of this patent is extended or adjusted under 35 U.S.C. 154(b) by 192 days.

(21) Appl. No.: 14/414,006

(22) PCT Filed: Jul. 2, 2013

(86) PCT No.: PCT/GB2013/051754
§ 371 (c)(1),
(2) Date: Jan. 9, 2015

(87) PCT Pub. No.: WO2014/009696
PCT Pub. Date: Jan. 16, 2014

(65) Prior Publication Data
US 2015/0204776 A1  Jul. 23, 2015

(30) Foreign Application Priority Data
Jul. 9, 2012 (GB) .................................. 1212147.1

(51) Int. Cl.
*G01R 27/08* (2006.01)
*G01N 17/04* (2006.01)
(Continued)

(52) U.S. Cl.
CPC .............. *G01N 17/04* (2013.01); *G01R 27/08* (2013.01); *G01N 1/00* (2013.01); *G01N 2201/00* (2013.01); *H01L 21/00* (2013.01)

(58) Field of Classification Search
CPC ...... G01N 1/00; G01N 2201/00; H01L 21/00; H01L 2221/00; G01R 1/00
See application file for complete search history.

(56) References Cited

U.S. PATENT DOCUMENTS 6,383,451 B1 * 5/2002 Kim .................... G01N 17/043
324/71.1
2008/0150555 A1 * 6/2008 Wang ................. G01D 5/35383
324/693
(Continued)

FOREIGN PATENT DOCUMENTS

GB   WO 2008125878 A1 * 10/2008 ........... G01N 17/043
WO       2008125878 A1    10/2008
(Continued)

OTHER PUBLICATIONS

International Preliminary Report on Patentability and Written Opinion received for Patent Application No. PCT/GB2013/051754, mailed on Jan. 22, 2015. 9 pages.
(Continued)

*Primary Examiner* — Jermele M Hollington
*Assistant Examiner* — Temilade Rhodes-Vivour
(74) *Attorney, Agent, or Firm* — Finch & Maloney PLLC

(57) ABSTRACT

A corrosion sensor for detecting the action of corrosive media on a metallic component when the sensor is mounted in the vicinity of the metallic component in use is disclosed. The sensor includes an electrically conducting corrodible element mounted on a non conducting substrate, the corrodible element being covered with a protective coating such as paint adapted to protect the corrodible element from corrosive media. The protective coating defines a temporary feature such as a paint defect which extends across the corrodible element and is designed to permit attack on the corrodible element by corrosive media after a predetermined period of time. The corrodible element comprises a pair of spaced tracks extending generally in a longitudinal direction and a series of corrodible tracks, each corrodible track extending generally in a lateral direction and forming an electrical connection between the spaced tracks. The temporary feature extends longitudinally, in the space between (Continued)

the pair of tracks, across a number of the corrodible tracks whereby to permit a corrosive attack on a number of the corrodible tracks after the predetermined period of time.

19 Claims, 2 Drawing Sheets

(51) Int. Cl.
*G01N 1/00* (2006.01)
*H01L 21/00* (2006.01)

(56) References Cited

U.S. PATENT DOCUMENTS

2012/0038377 A1* 2/2012 Hamann ................ G01N 27/00
 324/700
2012/0055810 A1* 3/2012 Zhou ...................... G01N 17/02
 205/775.5

FOREIGN PATENT DOCUMENTS

WO 2009141639 A1 11/2009
WO 2014009696 A1 1/2014

OTHER PUBLICATIONS

International Search Report and Written Opinion received for Patent Application No. PCT/GB2013/051754, mailed on Sep. 30, 2013. 11 pages.
GB Intellectual Property Office Search Report under Section 17(5) received for GB Patent Application No. 1212147.1 mailed Oct. 2, 2012. 3 pages.

\* cited by examiner

CORROSION SENSOR

This invention relates to corrosion sensors for detecting the action of corrosive media on a metallic material or component when mounted in the vicinity of the metallic component.

Corrosion is a problem which leads to high maintenance and repair overheads in many different industries. Prompt detection of problems caused by corrosion is necessary in order for effective mitigation strategies to be put in place. Thus various different methods of detecting corrosion in a metallic material have been developed.

A corrosion sensing strategy is proposed in the paper "Corrosion Sensors in Platform Management" by D. G. Dixon, M. C. Hebbron, S. J. Harris and A. Rezai and presented at the $1^{st}$ World Congress on Corrosion in the Military, 1 Jun. 2005. The authors propose a resistive sensor. The sensor disclosed by Dixon et al. is covered with a corrosion-inhibiting primer paint that is provided with a temporary feature in the form of an intentional defect in order to mimic, for example, the effect of a crack. The sensor is located on the structure to be monitored. At first, the defect will be protected from corrosive media by inhibitor species leaching from the paint, but, once the reservoir of inhibitor is exhausted, the sensor tracks will corrode, and a corresponding increase in the sensor resistance can be measured. Corrective action can then be taken. Such sensors can be termed "Inhibitor Depletion Sensors".

One particular prior-known corrosion sensor 100, of the inhibitor depletion type described above, is illustrated in FIG. 1 of the accompanying drawings. Sensor 100 comprises a substrate 110, a patterned conductive thin film 120 and paint substantially covering the substrate 110 and the patterned conductive thin film 120. The area covered by the conductive thin film is indicated by dense shading, whilst that covered by paint is indicated by more sparse shading. The film 120 is arranged in a ladder-like configuration such that there are three tracks 122, 123, 124 running between common terminal tracks 126 and 127. Three temporary features in the form of defects 132, 133, and 134 are introduced into paint 130, with each defect being provided at the location of one of the tracks 122, 123, and 124. The defects are areas where the protective layer of paint has been removed. However, in the case of an as-fabricated sensor, these areas remain temporarily protected from the effects of corrosion through the effect of inhibitor ions leaching out of the surrounding paint and onto the area of the defect. The tracks 122, 123, 124 are arranged to be wider than their respective defects 132, 133, 134 such that the entire exposed area beneath each defect consists of metallic track material. This arrangement contributes to a consistent wettability of the exposed areas to corrosive influence. Each defect is of a different size.

The conductive thin film 120 is formed on the substrate 110 by sputtering. The resultant sputtered film is then annealed in order to increase grain size, so that the film 120 resembles more closely the bulk metallic material that the sensor is intended to monitor. The paint is then applied over the conductive thin film using a mask to define the defects 132, 133, and 134.

In use, the resistance of the sensor 100 between points 150 is monitored over time. The resistance of the sensor remains approximately constant until the protective effect of inhibitor leaching from the paint around the largest defect 134 ceases because of exhaustion of the reservoir of inhibitor ions in the primer paint. At this point, the resistance will begin to increase as a result of corrosion depleting the amount of material in the conductive track 124. This, in turn, indicates when corrosion will begin to affect metal in other parts of the structure where there may be similar defects. By introducing a number of differently-sized defects, each over one rung of the ladder, a measure of the continuing effects of corrosion is obtained: the track beneath the largest defect 124 will corrode first, followed by that under the intermediate-sized defect 123, followed by that under the smallest-sized defect 122.

The above described sensor works well in principle. However it is not always easy to detect definite changes in voltage measured across the terminals 150 of the sensor exposed to corrosive media by cessation of inhibitor protection. This is because the inhibitor often fails to protect the element in its middle section, first. This means that a current path will still exist between the ends of each element, along side sections, after the middle section has corroded away. As the elements do not corrode away in a digital fashion, there will not generally be a clear step change in current flow through the element at the point of failure but rather a gradual change as the inhibitor starts to fail and corrosion gradually progresses across the element.

It is accordingly an aim of the present invention to mitigate at least some of the problems with prior known corrosion sensors.

According to a first aspect of the present invention, there is provided a corrosion sensor for detecting the action of corrosive media on a metallic component when the sensor is mounted in the vicinity of the metallic component in use, the sensor including an electrically conducting corrodible element mounted on a non conducting substrate, the corrodible element being covered with a protective coating adapted to protect the corrodible element from corrosive media, the protective coating defining a temporary feature extending across the corrodible element designed to permit attack on the corrodible element by corrosive media after a predetermined period of time, wherein the corrodible element comprises a pair of spaced tracks extending generally in a longitudinal direction and a series of corrodible tracks, each corrodible track extending generally in a lateral direction and forming an electrical connection between the spaced tracks, the temporary feature extending longitudinally, in the space between the pair of tracks, across a number of the corrodible tracks whereby to permit the said attack on a number of the corrodible tracks after the predetermined period of time.

The spaced pair of tracks may be generally parallel with each other and at least some of the series of corrodible tracks may be generally parallel with each other in order to provide predictable resistance of the tracks.

At least some, and preferably all, of the series of corrodible tracks may comprise substantially the same corrodible surface area as each other whereby to provide predictability of performance of the sensor.

For the same reason, the separation between at least some, and preferably all, adjacent corrodible tracks is substantially the same. Separation of the tracks can affect corrosion rate.

The temporary feature may terminate in the longitudinal direction at a track which does not form an electrical connection between the spaced tracks. In this way, unpredictability of performance due to unwanted "pooling" of paint and inhibitor can be avoided. Such pooling can preserve tracks protected in this way from corrosion for an indefinite period and make the sensor output unpredictable.

The spaced tracks may each define discontinuities along their length at positions staggered from the discontinuities in the opposed spaced track, whereby to direct electrical current longitudinally along the sensor element in a serpentine manner, traversing between the spaced tracks along defined numbers of corrodible tracks and thereby setting electrical resistance of the sensor element at a defined level. Resistance of the sensor can be increased by creating this serpentine current path whereby current is forced to pass through only a limited number of corrodible tracks, upon each passage between the spaced tracks.

The sensor may comprise a number of corrodible sensor elements arranged electrically in parallel between a pair of spaced terminal tracks. Such an arrangement could be used either to provide confirmation of the output of each sensor element, if all sensor elements are to the same design, or the temporary feature of at least two sensor elements may be adapted to permit corrosion attack on the corrodible tracks after substantially different predetermined times, for example by varying the sizes of the temporary features between sensor elements.

The protective coating may comprise a paint containing a corrosion inhibitor and a temporary feature may comprise a gap in the paint into which corrosion inhibitor will leach for a predetermined length of time.

Where sensor elements of different size are employed, an area of gap in the paint may vary in size between sensor elements in order to provide varying times to the onset of corrosion.

All tracks may be of substantially uniform thickness, measured in a direction generally normal to the plane of the sensor. This may have the advantage of permitting the sensor tracks to be formed in one layer and in one process.

In some circumstances it may be desired to have the electrical resistance of each sensor element substantially the same. In this way constant voltage step heights for the different sensor elements may be achieved. Equalisation of sensor element resistances can be achieved, for example, by adjusting the sectional area of the spaced tracks, in the respective sensor elements. This in turn could be achieved either by varying the area of the spaced tracks and/or by varying the thickness of the tracks. MEMS patterning of the tracks, using, for example photolithography for forming micro scale features can provide great versatility in this respect.

The width of gaps between corrodible tracks can be adjusted and this can be used to obviate the need for the thin film of the tracks to be annealed post-deposition. Annealing has previously been necessary to ensure that corrosion of the tracks occurs as rapidly as expected for bulk material, but it has been found that the same effect can be achieved using a narrow gap. It is also possible to further narrow the gap to ensure that the sensor reacts rapidly to any potentially harmful corrosion. Optionally, the width of the gaps is less than 15 µm. Empirical evidence suggests that gaps of this width lead to an increased rate of corrosion.

The provision of a number of sensor elements allows the corrosion sensor to provide a better indication of the average effects of corrosion on the bulk material, since, where only one sensor element is present, local effects unrepresentative of the behaviour of the bulk material in the presence of corrosive media may dominate the response of the sensor. Alternatively, where the sensor elements are formed with temporary features of a different width, the effects of corrosion can be monitored over an extended period of time. Corrodible tracks of different thicknesses may also be used in order to monitor the effects of corrosion over an extended period of time.

A high concentration of corrodible tracks per unit area of sensor, for example by the use of microlithography, enables the wettability of the corrodible tracks to remain approximately equal to that of the bulk metallic material on which the sensor is mounted, so that the sensor gives an accurate indication of the effects of corrosion on the bulk structure.

The invention extends, in a second aspect, to corrosion sensing apparatus comprising at least one corrosion sensor as defined above when coupled with means to monitor sensor resistance over time.

The invention extends, in a further aspect, to a component subject to corrosion incorporating either a corrosion sensor according to the first aspect of the invention or corrosion sensing apparatus according to the second aspect.

The component may be any component subject to corrosion but components upon which the sensor of the invention are likely to be used may be high value components such as aircraft wing or fuselage parts, ship parts or other parts subject to regular corrosive attack like oil pipelines, or drilling or other offshore rigs. The sensor of the invention is likely to be particularly useful on parts subject to corrosion but often difficult to access. Such parts may comprise aircraft wing or fuselage internal or external skin surfaces or be found in bays for landing gear or other equipment potentially exposed to corrosive conditions. Such corrosive conditions may be weather related or may occur if there is a failure with a system containing corrosive material, such as brake fluid.

Owing to the very small sizes possible with the sensor of the invention and its minimal projection from a surface to which it may be mounted, it is also particularly suitable for mounting on aerodynamic or hydrodynamic surfaces.

The above and further features of the invention are set forth in the appended claims and will now be described in further detail with reference to the accompanying drawings in which:

Figure 4:
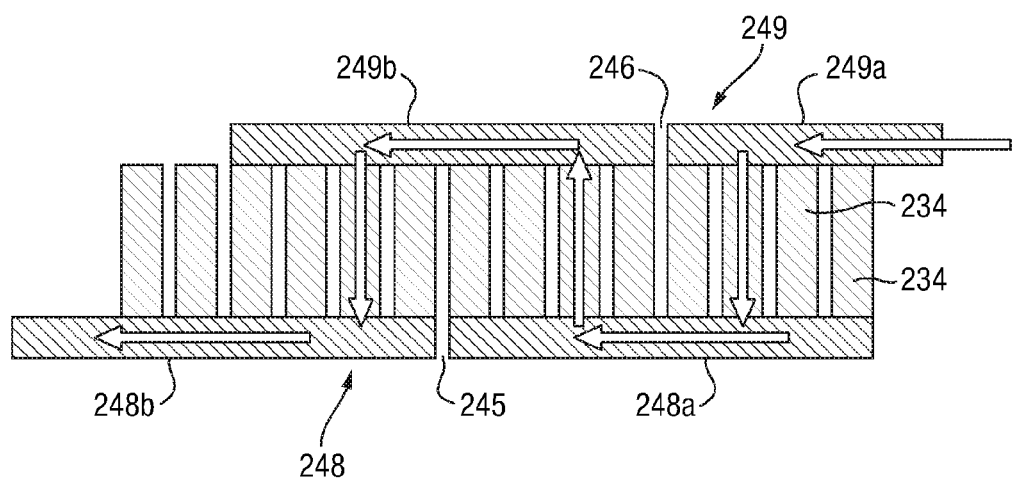

FIG. 4 is a schematic view of a set of corrodible tracks of a sensor element according to a second embodiment of the invention, and A corrosion sensor and corrosion sensing apparatus in accordance with the invention will now be described. Corrosion sensors and corrosion sensing apparatus according to the invention can be conveniently applied to aluminium and aluminium alloy structures, and are particularly applicable to such structures when painted with a corrosion inhibiting primer paint. It will, however, be clearly understood by those skilled in the art that the corrosion sensors could be trivially modified in order to function on other metallic structures.

The sensors include conducting corrodible tracks whose resistance increases on exposure to corrosive media when the cross sectional area of the track is corroded away. The sensors are arranged such that, when placed in situ in the vicinity of, adjacent to, or on a bulk component, the effects of exposure to corrosive media on the bulk component can be inferred from the measurable effects of exposure to the same corrosive media on the sensor. The sensors may be mounted in various locations and manners, for example by mounting between the plates of a joint between components, by adhesion to a component using a Mylar™ foil, etc.

Figure 2:
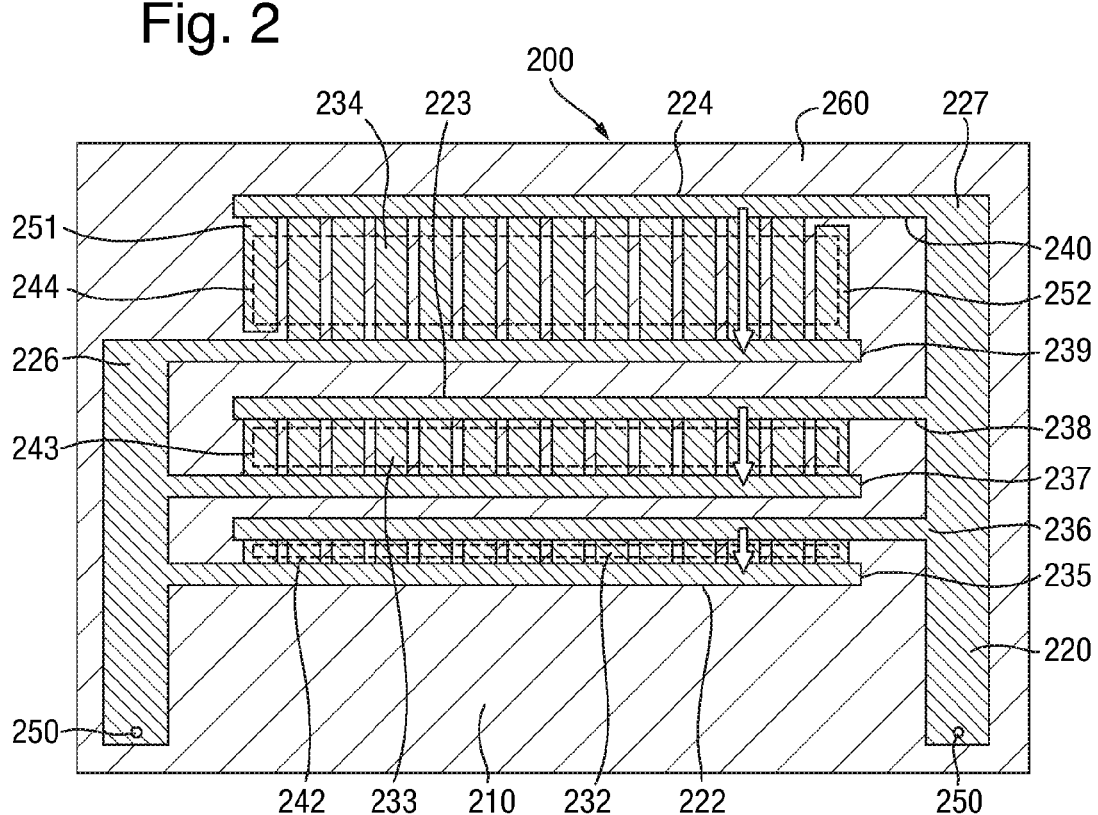
FIG. 2 is a schematic view of a corrosion sensor in accordance with the invention.

A corrosion sensor 200 in accordance with a first embodiment of the invention is shown in FIG. 2. Corrosion sensor 200 comprises a non conducting substrate 210, and a patterned conductive thin film 220. Film 220 is arranged in a ladder-like configuration such that there are three sensor elements 222, 223, 224 (that form the "rungs" for the ladder) running between common terminals 226, 227 (that form the "legs" for the ladder). In use of the sensor, electrical connections are made to the sensor from interrogating instrumentation via the common terminals 226, 227 at connection points 250.

In the embodiment shown in FIG. 2, the ladder-like configuration 220, and substrate 210 are covered over the majority of their surfaces by a coating of primer paint 260. The paint is of a type comprising a leachable corrosion suppressant. Such paints comprise corrosion inhibitors, such as chromate ions, that will leach out of the paint at or around any defects in the paint, thereby providing continued protection against corrosion even in the presence of minor defects in the paint. In FIG. 2, the conductive thin film is indicated by the densely shaded area, whilst the areas covered with paint are indicated by the more sparsely shaded area. The paint is of the same type as that covering the bulk structure which the corrosion sensor 200 is to monitor. In the present embodiment, a 25 µm thick coating of PR205, a primer paint commercially available from PRC DeSoto, is used. PR205 is a high-solids, chromate-loaded, epoxy-based primer. A suitable topcoat, such as HP03682, also available from PRC DeSoto, is then applied.

Rectangular temporary features in the form of unpainted areas or defects 242, 243, 244 are incorporated into the paint, and indicated in FIG. 2 in dashed outline. Each sensor element comprises a pair of spaced, generally parallel longitudinally extending tracks 235 and 236; 237 and 238, 239 and 240 and three series of laterally extending corrodible tracks 232, 233, 234, each of which forms an electrical connection between the pair of spaced tracks. Each defect 242, 243, 244 is formed over one of the sensor elements 222, 223 or 224 and extends longitudinally within the space between each pair of spaced tracks 235 and 236; 237 and 238; 239 and 240. In sensor element 224, the defect 244 terminates, at its longitudinal extremities, over tracks 251 and 252 which make no electrical connection between its pair of spaced tracks 239 and 240. The reason for this is described below in relation to FIG. 3. It will be observed that corrodible tracks 232 are shorter in length than tracks 333, which are themselves shorter than tracks 234. This arrangement has the effect of creating defects of differing width, as will be further discussed below.

On formation of the defects 242, 243, 244, inhibitor ions will leach out of the paint so as to continue to protect the corrodible tracks 232, 233, 234 from corrosive media. However, the continued protection is temporary, lasting only whilst there is a sufficient supply of inhibitor ions leaching from the paint surrounding the defect. Where the inhibitor comprises chromate ions, as in the present embodiment, it has been empirically determined that the protective effect persists until the concentration of chromate ions at the defect falls below approximately $10^{-3}$ mol/l. Once the inhibitor concentration falls below this level, the tracks will begin to corrode away, and their resistance will begin (measurably) to increase. The resistance of the tracks will continue to increase until they have corroded through, such that they can no longer form a conducting path between the spaced tracks. The amount of time taken for the tracks to corrode through will therefore depend, inter alia, upon the size of the defect (which will affect the concentration of inhibitor ions at the tracks); the concentration of inhibitor in the paint of the as-manufactured sensor, and the corrosivity of the environment in which the sensor 200 is placed.

As is shown in FIG. 2, each of the defects 242, 243, 244 is of a different size, and thus the duration of continued protection provided by each one of the defects is different. In particular, defect 244 is larger than defect 243, which in turn is larger than defect 242. And so, in the presence of corrosive media, tracks 234, beneath the largest defect, will corrode first, followed by tracks 233, located beneath the next-largest defect 243, followed finally by tracks 232, located beneath the smallest defect 242. Thus, by appropriate sizing of the defects 242, 243, 244, the largest could be arranged purely as a "check" to corrode rapidly and provide a confirmatory signal that the sensor 200 was functioning; the intermediate and smallest size defects could be arranged to indicate when it was necessary to fully inspect, and carry out any necessary repairs to, the structure on which the sensor was installed.

Figure 1:
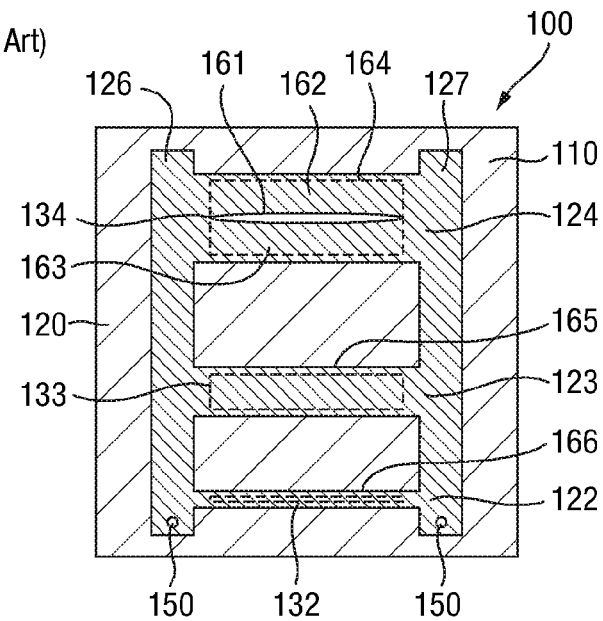
FIG. 1 is a schematic view of a prior art corrosion sensor.
Figure 3:
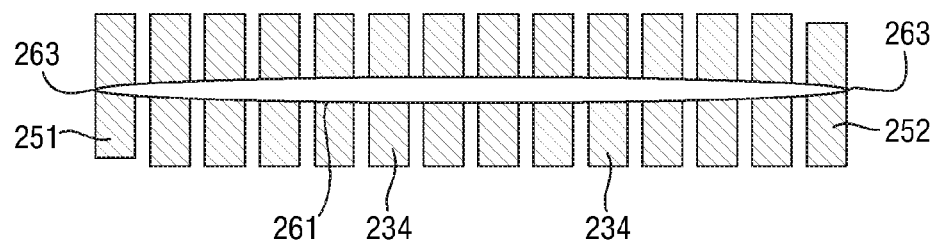
FIG. 3 is a schematic view of a set of corrodible tracks of a sensor element of the corrosion sensor of FIG. 2.

FIG. 3 shows, separated from their spaced tracks, just the corrodible tracks 234 of sensor element 224. Each track 234 is 4 mm long. Shown in a central region of the tracks is an oval area 261. This area 261 represents an area left exposed once corrosion inhibitor ions have ceased to protect the tracks. As will be seen, all the tracks are exposed and it is likely that all will start to corrode away and therefore increase in electrical resistance at about the same time. This feature is in contrast to the prior art sensor of FIG. 1 where an exposed area 161 of similar shape to the area 261 shown in FIG. 3 would leave considerable potentially uncorroded areas 162 and 163 which were still capable of conducting electricity and which would lead to uncertainty as to the state of corrosion of the track 124. Also, owing to the fact that edge areas 164, 165 and 166 of tracks 124, 123 and 122, respectively, will remain covered by paint, these areas of track will remain conductive. They will therefore reduce the possible voltage increase brought about by corrosion of the sensor and will reduce the responsiveness of the sensor.

The design of the sensor elements of the present invention will not lead to such uncertainty as to the time at which corrosion strikes; the rapid failure of each corrodible track in a sensor element, once inhibitor protection fails, should give a far more definite indication of the onset of corrosion. Very clear step changes in current flow occur, with the invention, with a number of step changes occurring per sensor element. It will be noted that the design of the sensor of the invention leaves no parts of the corrodible tracks covered by paint which are able to continue conducting electricity; the defects affect all corrodible tracks.

It will be seen that end tracks 262 are shorter than the rest. These tracks do not make electrical contact between the spaced tracks. The reason for this feature is that sometimes pooling of inhibitor can occur at end regions 263 of a paint defect and such pools can increase the time for which protection from corrosion will last. Continued conduction of electricity in these regions can give a false indication of lack of corrosion of the sensor. Equally, when these regions finally corrode through, corresponding increases in the voltage shown across the sensor terminals 250 can lead to confusion in interpreting the sensor readings.

A second possible scenario is that liquid from the environment can pool at the ends of the elements due to a step caused by the thickness of the paint. The presence of this liquid can initiate release of the inhibitor from the primer and can cause the supply of inhibitor to run out prematurely in these areas.

FIG. 4 shows a sensor element according to a second embodiment of the invention. It will be seen that spaced tracks 248, 249 each define discontinuities 245, 246 along their length, thereby dividing the spaced tracks into shorter lengths 248a, 248b, 249a and 249b. Because the discontinuities 245, 246 are staggered from one another, electrical current, shown by the arrows in the figure, is directed longitudinally along the sensor element in a serpentine manner. The current traverses between staggered pairs of the spaced tracks 249a to 248a, then 248a to 249b, then 249b to 248b, etc., etc., for further elongated sensor elements according to the invention. In the figure shown, current passes along four corrodible tracks 234, between each pair of spaced tracks. Thus, assuming the spaced tracks are of sufficiently low resistance as not to limit the resistance of the sensor, the electrical resistance of each sensor element will be set by the number of corrodible tracks 234 in a group linking an opposed pair of spaced tracks 249a to 248a, then 248a to 249b, then 249b to 248b, etc. As will be seen from FIG. 4, the number of corrodible tracks 234 in each group is four. The number of tracks in a group may be set at any desired number which is practicable for the size of sensor.

A particular advantage of the sensor 200 in comparison to the prior-known sensor 100 is that its overall resistance, as measured between the connection points 250, can be of order 600Ω to 1 kΩ, as compared to the maximum possible values of order only 1Ω possible with the prior art. This increase in the possible achievable resistance results from the fact that the tracks 232, 233, 234 of sensor 200 can be made much narrower than the corresponding tracks 122, 123, 124 of sensor 100. In contrast to the prior-known sensor 100, it is possible for the paint defects 242, 243, 244 to be significantly wider than the conducting tracks. The tracks 232, 233, 234 can all be of uniform width, and can be made as narrow as 1 μm if desired. Such a narrow track will corrode rapidly once the inhibitor supply from the paint is exhausted. Tracks of greater widths, for example in the range 5 to 10 μm, may be more robust, and, as will be appreciated by those skilled in the art, wider tracks can also be used if desired. However, in order to maintain as high a resistance as possible, it is preferable for the tracks to be kept as narrow as feasible for a particular sensor. The resistance of sensor 200 is thus two to three orders of magnitude larger than the maximum possible resistance obtainable with a sensor of the prior known type, such as sensor 100 described above. This large sensor resistance will be significantly greater than that of any cables or connectors used for connecting sensor 200 to any instrumentation necessary for monitoring of the resistance of sensor 200. Thus the signal-to-noise ratio for sensor 200 is significantly larger than that for sensor 100. Moreover, commercially-available off-the-shelf instruments and components are better suited to measurement of resistances of order 100Ω to 1000Ω than to measurement of resistances of order 1Ω. For example, a commonly available 20 mA current source would, in the case of sensor 100, provide a signal of amplitude 20 mV. Whilst such signals are measurable, robust measurement techniques are required where the sensor, in use, may be subjected to harsh environmental conditions, as will occur where the sensor is used to monitor corrosion of aircraft components. In contrast, a 20 mA current source used in conjunction with sensor 200 results in a signal of amplitude 2V to 20V, which is easily measurable, using robust, commercially-available, off-the-shelf instruments.

A further advantage of sensor 200 is that the overall wettability of the area underneath each defect remains very similar to that of the bulk material, since only a small part of the exposed area (that separating the conducting tracks) is of a different material to the bulk. It is well known that the rate of corrosion of a surface is related to the wettability of that surface. Moreover, the protective effect of inhibitor ions leaching out from surrounding paint will also be strongly dependent on the wettability of the surface beneath the defects. Therefore, it is important that the wettability of the exposed surface underneath the paint defects is kept as similar as possible to that of the bulk surface in order for the effect of corrosive media on the sensor 200 to be representative of the effect of corrosive media on the bulk.

When sensors according to the invention are mounted in situ, for example on a joint between two components on the internal frame of an aircraft, or on an external surface of a seaplane, an intermittent current signal is passed across common terminals and a voltage signal is measured. The resistance of the sensor can be calculated from the measured voltage signal. Typically, the measured resistance will be approximately constant for a period of time before beginning to increase as the tracks beneath the largest defect begins to corrode, once the reservoir of inhibitor around this defect is exhausted. The resistance of the sensor will then continue to increase until these tracks have corroded through, at which point the resistance becomes constant again. Once the tracks beneath the intermediate-sized defect begin to corrode, the resistance will again begin to increase, until the series of tracks of the second sensor element has corroded through. As will be clear to those skilled in the art, the resultant profile of resistance with time will have a stepped appearance, with each step occurring at the time at which one of the series of tracks of a sensor element has corroded through.

The sensor 200 is fabricated in a similar manner to prior art sensors. The thin film layers from which the tracks are made are deposited on the substrate by sputtering. In order to improve the degree to which the corrodible characteristics of the tracks mimic the bulk alloy, the thin film layer can be annealed following sputtering to encourage growth of metallic grains within the layer to produce a thin film which is essentially a two-dimensional array of metallic grains. Enhancing the grain size after sputtering by annealing enhances the capability of the sensors to detect localised corrosion, at the early stages of its growth. Since localised corrosion initiates at specific sites such as grain boundaries, specific intermetallic phases etc., production of thin films of metal alloys with similar compositions of intermetallic phases and grain boundaries to the bulk metal enhances detection of localised corrosion. By subsequent photolithographic patterning, the films are structured into the above described track forms.

The annealing step may be omitted. Because the sensitivity to corrosion of the tracks can be controlled, to an extent, by adjusting the width of the gaps between the corrodible tracks, it is possible, empirically, to adjust the width of the gaps such that the sensitivity to corrosion of a non-annealed corrodible track can be increased to be equal to that of an annealed track. This method involves fewer manufacturing steps and sensors can therefore be fabricated more simply than prior art corrosion sensors.

The thickness of the corrodible tracks is selected in accordance with the material from which the tracks are formed and the type of application. For example, in a marine environment, the rate of corrosion is relatively high, and therefore a relatively thick film is used. For an aluminium alloy, corrodible tracks in the region of 50 μm to 500 μm in thickness are used. For use in less corrosive environments, higher sensitivity to corrosion is required, and therefore thinner films are used. For non-marine aircraft components, the thickness of the corrodible tracks is preferably between 0.5 μm and 10 μm, for example approximately 1.5 μm.

The paint can be applied by spraying, whilst the defects in the paint can be formed using a physical mask such as masking tape. Alternatively, chemical and dry etching techniques are possible. One etchant for use with PR205 is ethylene glycol. Using these techniques, defects having widths between 50 µm and 8 mm can be fabricated.

In envisaged applications, the bulk metal material to be mimicked is a metallic alloy and the material used for the corrodible tracks is preferably an alloy having alloying constituents in similar proportions to the bulk alloy being mimicked. It has been found that the proportion of each alloying constituent of the track material is preferred to be accurate to within 3%, more preferably to within 1%, of the total constituents of the bulk alloy. Constituents having a proportion of less than 1% of the bulk alloy may either be present in a similar proportion, or omitted.

In embodiments where the sensor is to be used in a health monitoring system for aircraft, the corrodible tracks are made of an aluminium alloy, such as an aluminium copper alloy, an aluminium silicon alloy, an aluminium silicon copper alloy, etc. The material used for the corrodible tracks is preferably an alloy which closely resembles in composition one of the aluminium alloys used in the aviation components.

For 2000 series aluminium alloy, the track alloy is an aluminium-copper alloy having a copper constituent in the region of 2% to 8%, preferably approximately 5%, of the alloy mass.

For 4000 series aluminium alloy, the track alloy is an aluminium-silicon alloy having a silicon constituent in the region of 4% to 20%, preferably approximately 12%, of the alloy mass.

For 5000 series aluminium alloy, the track alloy is an aluminium-magnesium alloy having a magnesium constituent in the region of 2% to 8%, preferably approximately 5%, of the alloy mass.

For 6000 series aluminium alloy, the track alloy is an aluminium-magnesium-silicon alloy having magnesium and silicon proportions in the region of 0.3% to 1.2%, of the alloy mass.

For 7000 series aluminium alloy, the track alloy is an aluminium-zinc alloy having a zinc constituent in the region of 2% to 8%, preferably approximately 5%, of the alloy mass.

For 8000 series aluminium alloy, the track alloy is an aluminium-lithium alloy having a lithium constituent in the region of 1% to 4%, preferably approximately 2%, of the alloy mass.

Note that other alloying constituents, in lesser proportions to those specifically mentioned, may also be present in the alloys from which the tracks are made. These may include one or more of magnesium, copper, manganese, silicon, iron, zinc, lithium, titanium, chromium, vanadium, zirconium, etc.

The substrate can be formed from any suitable insulating material on which a thin film of the track material can be deposited. For example, Mylar™' or polyimide can be used. Alternatively, a conducting substrate coated with an insulating layer of, for example, polyimide could be used.

Variations and modifications are possible without departing from the scope of the invention, which is defined in the accompanying claims. These will be obvious to those skilled in the art. For example, in the above it has been described to use straight spaced tracks and corrodible tracks, it will be understood that it is possible to use tracks of a different configuration, such as serpentine tracks.

Furthermore, whilst, three sensor elements running between the spaced terminal tracks have been described, it will be appreciated that any number of sensor elements could be used. An indication of when corrosion has begun to have an effect can be obtained from a sensor having just one sensor element, whilst a sensor having a larger number of sensor elements can be used to give a better indication of the progression of the effects of corrosion on a structure over a more extended period of time. Clearly, as the number of sensor elements increases, the resistance of the sensor will decrease, but it is expected that this effect is unlikely to be significant for up to ten sensor elements.

The resistance of sensors in accordance with the invention can be measured using a Wheatstone bridge. Such methods enable the resistance of the sensor to be accurately measured through sensing a null in the bridge current once balance is achieved. Conveniently, at least some of the bridge resistors can be fabricated on the sensor substrate.

It is possible to design the layout of the sensor, above, such that the substrate is almost entirely covered with the conductive thin film. This ensures that paint will stick to the sensor more uniformly. As those skilled in the art will appreciate, paint will not stick to the material of the substrate to the same degree that it will to the conductive thin film. Therefore, by ensuring that the substrate is substantially entirely covered with the conductive film, the sensor will mimic more closely the behaviour of the bulk structure.

It will be necessary, where the sensors are to be retro-fitted to existing structures, to mix paint with an appropriate inhibitor ion concentration, in order to mimic the effect of the age of the paint on the structure. Paints comprising corrosion inhibitors are widely available from a number of manufacturers, including Akzo Nobel, Anac, and Indestructible Paints. Paints comprising corrosion inhibitors other than chromate ions are expected to become more widely used in the future because of the potential hazards of chromate-containing paints. It may be desirable to anodise the surface of the conductive film, or to apply a conversion coating prior to applying the paint. Such a treatment enhances adherence of the paint to the metal surface. Conversion coating can be achieved using Alodine.

It is envisaged that the present invention will find particular application in the field of aviation. However, the corrosion sensors of the present invention can be easily modified for use in any number of structures, provided that the paint used to cover the substrate, and the conductive material used to form the patterned conductive thin film, are chosen to suitably mimic the behaviour of the bulk structure in the presence of corrosive media. Alternatively, conductive materials and paints could be used that do not mimic the behaviour of a bulk structure, but that can be used to give an indication of the corrosivity of a particular environment as a reference value.

The invention claimed is:

1. A corrosion sensor for detecting the action of corrosive media on a metallic component when the sensor is mounted in the vicinity of the metallic component in use, the sensor comprising:
   an electrically conducting corrodible sensor element mounted on a non-conducting substrate,
   the sensor element being covered with a protective coating adapted to protect the sensor element from corrosive media,
   the protective coating defining a temporary feature extending across the sensor element designed to permit attack on the sensor element by corrosive media after a predetermined period of time,
   wherein the sensor element comprises a pair of spaced tracks extending generally in a longitudinal direction and a series of corrodible tracks, each corrodible track extending generally in a lateral direction and forming an electrical connection between the spaced tracks, the temporary feature extending longitudinally, in the space between the pair of tracks, across a number of the corrodible tracks whereby to permit the said attack on a number of the corrodible tracks after the predetermined period of time.

2. The corrosion sensor as in claim 1, wherein the spaced pair of tracks are generally parallel with each other and at least some of the series of corrodible tracks are generally parallel with each other.

3. The corrosion sensor as in claim 1, wherein at least some of the series of corrodible tracks comprise substantially the same corrodible surface area as each other.

4. The corrosion sensor as in claim 1, wherein the separation between at least some adjacent corrodible tracks is substantially the same.

5. The corrosion sensor as in claim 1, wherein the temporary feature terminates in the longitudinal direction at a track which does not form an electrical connection between the spaced tracks.

6. The corrosion sensor as in claim 1, wherein the spaced tracks each define discontinuities along their length at positions staggered from the discontinuities in the opposed spaced track, whereby to direct electrical current longitudinally along the sensor element in a serpentine manner, traversing between the spaced tracks along defined numbers of corrodible tracks and thereby to set electrical resistance of the sensor element at a defined level.

7. The corrosion sensor as in claim 1, comprising a number of sensor elements arranged electrically in parallel between a pair of spaced terminal tracks.

8. The corrosion sensor as in claim 7, wherein the temporary feature of at least two sensor elements is adapted to permit corrosion attack on the corrodible tracks after substantially different predetermined times.

9. The corrosion sensor as in claim 1, wherein the protective coating comprises a paint containing a corrosion inhibitor and in which a temporary feature comprises a gap in the paint into which the corrosion inhibitor will leach for a predetermined length of time.

10. The corrosion sensor as in claim 8, wherein the protective coating comprises a paint containing a corrosion inhibitor and in which a temporary feature comprises a gap in the paint into which the corrosion inhibitor will leach for a predetermined length of time, and wherein an area of the gap in the paint varies in size between sensor elements.

11. The corrosion sensor as in claim 1, wherein all tracks are of substantially uniform thickness, measured in a direction generally normal to the plane of the sensor.

12. The corrosion sensor as in claim 7, wherein the electrical resistance of each sensor element is substantially the same.

13. A corrosion sensing apparatus including at least one corrosion sensor as in claim 1, when operatively coupled with instrumentation configured to monitor sensor resistance over time.

14. A component subject to corrosion when paired with a corrosion sensor as in claim 1.

15. A component subject to corrosion incorporating corrosion sensing apparatus as in claim 13.

16. An aircraft wing or fuselage incorporating at least one component as in claim 14.

17. An aircraft wing or fuselage incorporating at least one component as in claim 15.

18. A corrosion sensor for detecting the action of corrosive media on a metallic component when the sensor is mounted in the vicinity of the metallic component in use, the sensor comprising:
an electrically conducting corrodible sensor element mounted on a non-conducting substrate,
the sensor element being covered with a protective coating adapted to protect the sensor element from corrosive media,
the protective coating defining a temporary feature extending across the sensor element designed to permit attack on the sensor element by corrosive media after a predetermined period of time,
wherein the sensor element includes a pair of spaced tracks extending generally in a longitudinal direction and a series of corrodible tracks, each corrodible track extending generally in a lateral direction and forming an electrical connection between the spaced tracks,
wherein the temporary feature extends longitudinally, in the space between the pair of tracks, across a plurality of the corrodible tracks whereby to permit the said attack on a number of the corrodible tracks after the predetermined period of time, and
wherein the temporary feature terminates in the longitudinal direction at a track which does not form an electrical connection between the spaced tracks.

19. A corrosion sensor for detecting the action of corrosive media on a metallic component when the sensor is mounted in the vicinity of the metallic component in use, the sensor comprising:
an electrically conducting corrodible sensor element mounted on a non-conducting substrate,
the sensor element being covered with a protective coating adapted to protect the sensor element from corrosive media,
the protective coating defining a temporary feature extending across the sensor element designed to permit attack on the sensor element by corrosive media after a predetermined period of time,
wherein the sensor element includes a pair of spaced tracks extending generally in a longitudinal direction and a series of corrodible tracks, each corrodible track extending generally in a lateral direction and forming an electrical connection between the spaced tracks,
wherein the spaced tracks each define discontinuities along their length at positions staggered from the discontinuities in the opposed spaced track, whereby to direct electrical current longitudinally along the sensor element in a serpentine manner, traversing between the spaced tracks along defined numbers of corrodible tracks and thereby to set electrical resistance of the sensor element at a defined level.

* * * * *